(12) United States Patent
Barron et al.

(10) Patent No.: US 7,294,367 B2
(45) Date of Patent: *Nov. 13, 2007

(54) BIOLOGICAL LASER PRINTING VIA INDIRECT PHOTON-BIOMATERIAL INTERACTIONS

(75) Inventors: Jason Barron, Alexandria, VA (US); Bradley R. Ringeisen, Alexandria, VA (US); Heungsoo Kim, Fairfax, VA (US); Peter Wu, Ashland, OR (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 155 days.

This patent is subject to a terminal disclaimer.

(21) Appl. No.: 10/863,850

(22) Filed: Jun. 4, 2004

(65) Prior Publication Data

US 2005/0018036 A1    Jan. 27, 2005

Related U.S. Application Data

(60) Provisional application No. 60/476,377, filed on Jun. 6, 2003, provisional application No. 60/542,841, filed on Feb. 10, 2004.

(51) Int. Cl.
| | |
|---|---|
| *H05B 7/00* | (2006.01) |
| *G01N 33/543* | (2006.01) |
| *G01N 33/544* | (2006.01) |
| *G01N 33/551* | (2006.01) |
| *G01N 33/552* | (2006.01) |

(52) U.S. Cl. .................. 427/596; 427/595; 435/518; 435/524; 435/527; 435/535

(58) Field of Classification Search .............. 436/518, 436/524, 527, 535; 427/595–6
See application file for complete search history.

(56) References Cited

U.S. PATENT DOCUMENTS

| | | | | |
|---|---|---|---|---|
| 3,600,319 | A * | 8/1971 | Gedge et al. | 510/320 |
| 4,886,681 | A * | 12/1989 | Clabes et al. | 427/525 |
| 4,952,294 | A * | 8/1990 | Collins et al. | 204/192.11 |
| 4,987,006 | A * | 1/1991 | Williams et al. | 427/597 |
| 5,156,938 | A | 10/1992 | Foley | |
| 5,171,650 | A | 12/1992 | Ellis | |
| 5,292,559 | A * | 3/1994 | Joyce et al. | 427/597 |

(Continued)

FOREIGN PATENT DOCUMENTS

WO    WO 200044960 A1 *    8/2000

OTHER PUBLICATIONS

Barron et al., "Printing of protein microarrays via capillary-free fluid jetting mechanism", Proteomics, 2005, vol. 5, pp. 4138-4144.*

(Continued)

*Primary Examiner*—Long V. Le
*Assistant Examiner*—Unsu Jung
(74) *Attorney, Agent, or Firm*—John J. Karasek; Joseph T. Grunkemeyer

(57) ABSTRACT

A method of laser forward transfer is disclosed. Photon energy is directed through a photon-transparent support and absorbed by an interlayer coated thereon. The energized interlayer causes the transfer of a biological material coated thereon across a gap and onto a receiving substrate.

44 Claims, 12 Drawing Sheets

U.S. PATENT DOCUMENTS

| | | | |
|---|---|---|---|
| 5,308,737 A | | 5/1994 | Bills |
| 5,324,591 A | | 6/1994 | Georger, Jr. |
| 5,725,989 A | * | 3/1998 | Chang et al. ............... 430/201 |
| 5,780,971 A | * | 7/1998 | Dawson et al. ............... 315/39 |
| 5,958,268 A | * | 9/1999 | Engelsberg et al. .... 219/121.84 |
| 5,959,297 A | * | 9/1999 | Weinberg et al. ........... 250/288 |
| 6,008,052 A | * | 12/1999 | Davis et al. .................. 436/10 |
| 6,177,151 B1 | | 1/2001 | Chrisey |
| 6,284,117 B1 | * | 9/2001 | Smolko et al. ............. 204/543 |
| 6,403,367 B1 | * | 6/2002 | Cheng et al. ............ 435/287.1 |
| 6,541,420 B2 | * | 4/2003 | Yamamoto et al. ......... 503/227 |
| 6,805,918 B2 | * | 10/2004 | Auyeung et al. ........... 427/596 |
| 6,815,015 B2 | * | 11/2004 | Young et al. ............... 427/596 |
| 6,905,738 B2 | * | 6/2005 | Ringeisen et al. ........... 427/596 |
| 6,936,311 B2 | * | 8/2005 | Ringeisen et al. .......... 427/596 |
| 2002/0015958 A1 | * | 2/2002 | Audeh et al. .................. 435/6 |
| 2002/0048765 A1 | * | 4/2002 | Shao et al. .................... 435/6 |
| 2002/0071901 A1 | | 6/2002 | Ringeisen |
| 2002/0122898 A1 | | 9/2002 | Ringeisen |
| 2002/0173033 A1 | * | 11/2002 | Hammerick et al. ..... 435/305.2 |
| 2004/0247777 A1 | | 12/2004 | Ringeisen et al. |

OTHER PUBLICATIONS

Ringeisen et al., "Generation of mesoscopic patterns of viable *Escherichia coli* by ambient laster transfer", Biomaterials, 2002, vol. 23, pp. 161-166.*

Ringeisen et al., "Picoliter-scale protein microarrays by laser direct write", Biotechnol. Prog., 2002, vol. 18, pp. 1126-1129.*

Tolbert et al, "Laser Ablation Transfer Imaging Using Picosecond Optical Pulses: Ultra-High Speed, Lower Threshold and High Resolution", Journal of Imaging Science and Technology, Sep./Oct. 1993, pp. 485-489, vol. 37, No. 5.

* cited by examiner

BIOLOGICAL LASER PRINTING VIA INDIRECT PHOTON-BIOMATERIAL INTERACTIONS This application claims the benefit of U.S. Provisional Patent Application No. 60/476,377, filed on Jun. 6, 2003 and U.S. Provisional Patent Application No. 60/542,841, filed on Feb. 10, 2004. All applications named are incorporated by reference. The U.S. Patent Application to Ringeisen et al., titled "Biological Laser Printing from Tissue via Indirect Photon-Biomaterial Interactions," designated NC 96,075, filed on the same day as the present application is also incorporated by reference.

BACKGROUND OF THE INVENTION

1. Field of the Invention

The invention is generally related to methods of laser and/or photon transfer.

2. Description of the Prior Art

Direct write technologies have gained popularity with the increased interest in biological sensors and microarrays, and the push for engineered tissues to replace organ transplants. These techniques allow for increased ability to manipulate biological materials in very small volumes with much better accuracy than has been previously possible. Some of the most promising techniques for use in controlling and transferring biological materials are matrix assisted pulsed laser evaporation direct write (MAPLE DW, see U.S. Pat. No. 6,177,151 to Chrisey et al. (all referenced patents, patent applications and publications are incorporated herein by reference), dip-pen nanolithography (DPN), scanning probe microscopy (SPM), microcontact printing (MCP), and laser guidance direct write.

MAPLE DW focuses a pulsed laser source at the interface of a quartz "ribbon" (analogous to a typewriter, it is usually a quartz slide with a coating containing a mixture of a matrix support material and the biological materials of interest) to cause the ablation of a small amount of the interfacial matrix material, which then causes the remaining bulk matrix and biological material to be expelled from the ribbon in a bubble-jetting effect. The expelled material travels through-space, away from the laser and ribbon to a receiving substrate. This results in a spot of transferred material approximately 100 µm in diameter with pL scale volumes. MAPLE DW has limited applications or inherent limitations due to the physical properties of the biological materials and surrounding media needed to ensure accurate pattern formation. Specifically, MAPLE DW requires that a mixture of transfer material and a matrix material be presented to the laser source. The matrix must be of higher volatility than the transfer material and strongly absorb the incident radiation. In addition, the reproducibility of the technique can be low due to inconsistencies in the parameters necessary for ablation of the matrix material. Also, because the absorptivity of certain matrix materials is quite low, there is the potential for damage to biological materials from direct and indirect interaction with the incident laser radiation.

DPN and SPM are direct-write techniques that offer the possibility of writing very small amounts of material. DPN has been used to write lines of collagen 30-50 nm in width. Both these techniques have been used to lay down patterns of organic adhesion molecules, which are then used for adhesion of biological molecules of interest. This leads to difficulty in patterning multiple biological material types and difficulty in rapid design of micro-scale constructs.

MCP techniques utilize biomaterial coated polymer stamps to transfer biomaterials to more adhesive substrates. It is possible to obtain sub-micron features using MCP, but there is little control over the amount of material transferred. It is possible that different materials could be patterned using multiple stampings, but this could lead to possible contamination of stamps and has inherent limitations in the proximity of the different material types. Also, MCP is dependent on biomaterial-substrate adhesion, and therefore not universal to all substrate materials.

Laser-guided DW uses a "loose" form of optical trapping to guide cells along the beam axis and to a receiving substrate. The use of a low NA lens allows for a continuous stream of cells or molecules to be transferred to a target substrate. This technique allows for manipulation and placement of individual cells, but has limitations in the fact that it can take hours to write a moderate number of cells. In addition there is the potential for DNA damage from the extended time that cells or other biological materials are exposed to the laser beam.

Laser transfer of biological materials presents a challenge due to the fragility of many biological materials. They can be harmed by shear stress when they are removed from the target substrate and by impact stress when they land on the receiving substrate. DNA in particular can be uncoiled by such stresses. Heat can denature many biological materials. UV damage can also result when a UV laser is used.

In some other techniques, the target substrate is coated with several layers of materials. The outermost layer, that is, the layer closest to the receiving substrate, consists of the material to be deposited and the innermost layer consists of a material that absorbs laser energy and becomes vaporized, causing the outermost layer to be propelled against the receiving substrate. Variations of this technique are described in, for example, the following U.S. patents and publications incorporated herein by reference: U.S. Pat. No. 5,308,737 to Bills et al., U.S. Pat. No. 5,171,650 to Ellis et al., U.S. Pat. No. 5,256,506 to Ellis et al., U.S. Pat. No. 4,987,006 to Williams et al., U.S. Pat. No. 5,156,938 to Foley et al. and Tolbert et al., "Laser Ablation Transfer Imaging Using Picosecond Optical pulses: Ultra-High Speed, Lower Threshold and High Resolution" Journal of Imaging Science and Technology, Vol. 37, No. 5, September/October 1993 pp. 485-489. A disadvantage of these methods is that they can still expose the material to be deposited to high amounts of energy that may not be suitable for biological materials.

SUMMARY OF THE INVENTION

The invention comprises a method for printing materials comprising the steps of: providing a receiving substrate, providing a target substrate, providing a source of photon energy, and directing the photon energy. The target substrate comprises a photon-transparent support, a photon-absorbent interlayer coated on the support, and a transfer material comprising a biological material coated on top of the interlayer opposite to the support. The photon energy is directed through the transparent support so that it strikes the interlayer. A portion of the interlayer is energized by absorption of the photon energy, which causes a transfer of a portion of the transfer material across a gap between the target substrate and the receiving substrate and onto the receiving substrate

DETAILED DESCRIPTION OF THE EXAMPLE EMBODIMENTS

Figure 1:
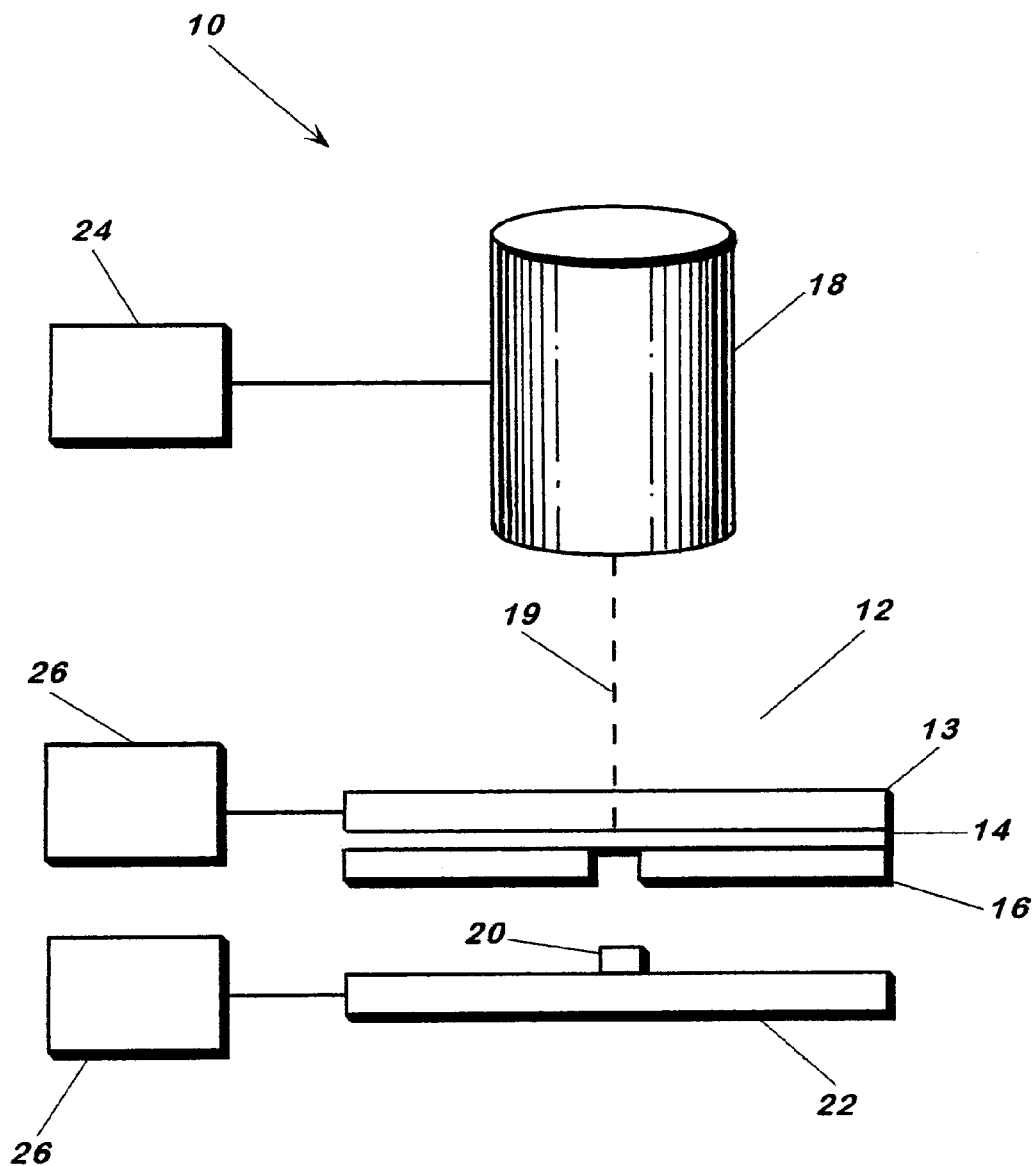
FIG. 1 schematically illustrates an apparatus used to perform the method of the invention.

The invention provides a method for transfer of biological materials that can allow for control of material placement and volume, and can prevent damage to biological structure and function. These criteria are relevant to designing new processes and techniques for tissue engineering, microfluidic cell and protein-based microsensors, genomic and proteomic microarrays and nanoarrays, biological or chemical sensors, and cell-specific culturing applications.

The invention uses photon energy, such as a laser, incident upon an interlayer to induce a biological material to be forward-transferred through space to a receiving substrate, microns to millimeters away from the target support. This eliminates the requirement of a laser-matrix interaction as in MAPLE DW. The interlayer converts photon energy into thermal energy. Laser absorption and energy conversion by the interlayer results in the removal of a three dimensional pixel of biomaterial from the target though one of a number of mechanisms, and propelling an aliquot of biomaterial through air towards a receiving substrate. The amount of biomaterial transferred in a single pixel is a function of several factors including the laser spot size, the thickness of the biomaterial layer on the ribbon, and the laser fluence. The method is independent of the type of biological material present. Material deposition may be done at ambient temperatures under room conditions. The technique allows for transfer of very small transferred volumes (<pL scale), spot sizes as small as 20-50 μm, and has the demonstrated ability to deposit patterns of single cells.

The method can have several key advantages over MAPLE DW. Laser interaction with the transfer layer is indirect. This means that virtually any material in a wet or dry condition can be transferred without having to consider its ability to absorb incoming radiation, which is an imperative requirement for a successful MAPLE DW transfer. This also means that laser absorption can be essentially constant across materials and therefore, accurate transfers can be easier and reproducibility can be greatly increased. Further, interaction of the laser with the transferred biological material is substantially eliminated. This reduces the possibility of genetic or biological damage from the relatively high energies of the focused laser beam. As the biological layer also acts as the laser absorption layer in MAPLE DW, transfer conditions can vary greatly due to changes in the biological layer, altering the laser adsorption properties that are central to achieving the successful transfer of material. Calculations show that much of the laser energy (>99%) passes completely through the liquid, raising the possibility that the UV laser light could damage the biological material (Parkinson et al., "Absorption cross-section measurements of water vapor in the wavelength region 181-199 nm," *Chem. Phys.*, 204(31), 31 (2003)). Single and double strand comet assays have shown little to no observable genetic damage to the cells, but UV exposure could still hinder other aspects of biological activity via radical formation and cellular response to the UV. Finally, controlling the MAPLE DW transfer process for biological materials is more difficult, due to their poor UV absorption properties (aqueous mediums). In essence, the laser is absorbed by and could cause vaporization through the entire volume of material with which it interacts. This can lead to problems in attaining reproducible results.

The technique allows for the stepwise writing of biological materials without the use of masks or patterning techniques. It can have the ability to write materials in a three-dimensional manner (layer-by-layer) and to write onto non-planar surfaces. Because of the transfer mechanism, it is possible to transfer virtually any biological material, independent of physical properties such as phase, viscosity, homogeneity, light absorbance, and volatility. This method also can allow for rapidly transferring a large number of cells of the same type or a variety of types in any order and in close proximity. With no direct contact with the receiving substrate, there is less concern about contamination and with the relatively small transfer volumes, it is possible to obtain very accurate transfer placement.

FIG. 1 schematically illustrates an apparatus 10 that may be used to perform the method of the invention. The apparatus 10 includes a target substrate 12, which comprises a photon-transparent support 13 having an interlayer 14 coated thereon, and a transfer material 16 coated on the interlayer. The transfer material comprises a biological material. A pulsed laser 18 sends laser pulses 19 into the target substrate and through the support. The pulses are absorbed by the interlayer, which causes a portion 20 of the transfer material to be transferred to a receiving substrate 22. The target substrate, the receiving substrate, and the photon energy source can be moveable with respect to each other.

Control of the beam can be done via an optical stage 24 and manipulation of the target and receiving substrates can be accomplished by computer-controlled stages 26 and CAD/CAM programs that allow for design of complex shapes, and patterns and the deposition of different materials in a precise and ordered manner. Independent manipulation of ribbon and substrate can be done via a computer-controlled stage.

The source of photon energy may be any photon source that provides sufficient photons to cause the transfer. A suitable photon source is a laser, such as a continuous laser or a pulsed laser. The fluence of a pulsed laser should be chosen such that the transfer is accomplished without causing any undesirable damage to the biological material, with or without removal of the interlayer. Pulsed lasers are commercially available within the full spectral range from UV to IR. Typically, such lasers emit light having a wavelength in the range of about 157-10600 nm, a pulsewidth of about $10^{-12}$-$10^{-6}$ second and a pulse repetition frequency of about 0 to greater than 100,000 Hz. Examples of suitable lasers include, but are not limited to, excimer lasers operating at 193 and 248 nm and frequency quadrupled or tripled Nd:YAG laser operating at 266 and 355 nm. Suitable ranges of fluence include, but are not limited to, from about 1 to about 1000 mJ/cm$^2$, at least about 0.1 mJ/cm$^2$, and at least about 1 nJ/cm$^2$. A 193 nm Lambda Physik 300 ArF excimer laser or a frequency tripled Nd:YAG laser (355 nm) may be used for transfers. The dimensions of the laser energy can be controlled by any means known in the art so that only a precisely defined area of the target substrate is exposed to the laser energy and so that only a precisely defined portion of the transfer material is exposed. The laser energy can be focused through an objective or lens to narrow the beam and expose a smaller portion of transfer material. The beam can be focused down to an approximately 10-150 μm spot size at the ribbon interlayer. This increases the possible resolution of the deposited biological material. Other suitable photon sources include, but are not limited to, a flash lamp and a maser. A flash lamp may be more divergent and require optics to force the light to propagate parallel/co-linear.

The photon-transparent support can be made of any material that is substantially transparent to the particular photons that make up the photon energy. Suitable support materials include, but are not limited to, quartz, a glass, a salt, and a polymer. Quartz is suitable when UV photons are used.

The interlayer can be made of any material that significantly absorbs the photon energy, and may be inorganic. Suitable interlayer materials include, but are not limited to, a metal, a metal oxide, titanium metal, titanium dioxide, chrome, molybdenum, gold, and a polymer, and may comprise more than one layer. Suitable ranges of thickness of the interlayer include, but are not limited to, 10 Å to 10 μm and 5 to 100 nm.

The transfer material can be coated on the support by numerous techniques, including but not limited to spin coating, spray coating, dipping, doctor blading, roller coating, and screen-printing, and may be in the form of a powder, solid, liquid or gel. The surface of the target substrate can be broken into separate regions with different transfer materials in order to be able to deposit different biological materials without having to change the target substrate.

The biological material can be any material of a biological nature, whether naturally occurring or engineered, or synthetic equivalents thereof, include, but are not limited to, proteins, hormones, enzymes, antibodies, DNA, RNA, nucleic acids, aptamers, antigens, lipids, oligopeptides, polypeptides, cofactors, polysaccharides, and biocompatible materials such as tissue scaffolding material, ceramic, or polymer. The biological material can be cells, living or non-living. The cells may be stained cells and may be prokaryotic or eukaryotic. Living cells may remain living on the receiving substrate after the transfer is complete, or the cells may be dead. The cells may be dried or lyophilized. The cells may also be in a solution that is evaporated during the transfer, which may also be used as a method of drying cells, although survival rates may be lower. This evaporation or drying may not be from the heated interlayer but from the air currents during transit from the target to the receiving substrate. A cushioning coating on the receiving substrate may help the cells to survive the impact with the receiving substrate. Suitable cushioning coatings include, but are not limited to, hydrogel and polymers, which may be at least 10 μm thick, and aqueous solutions. There can be minimal to no DNA strand breaks in the transferred cells. The receiving substrate may be a microtitre plate, or may be a living substrate such as an animal or plant.

In some embodiments, the transfer material also comprises a biomatrix along with the biological material. The biomatrix can be any material that is compatible with the biological material and that does not prevent the transfer. The biomatrix may contribute to sustaining the biological activity of the biological material. The biological material and the biomatrix may mixed together or in separate layers. Suitable biomatrices include, but are not limited to, cell medium, water, glycerol, a mixture of water and glycerol, mammalian serums, buffered salt solution, biocompatible polymers, extracellular matrix, organic tissue scaffolding, inorganic tissue scaffolding, biocompatible surfactants, Tween, sodium dodecyl sulfate, cell medium, cell nutrient, natural hydrogel, synthetic hydrogel, surfactant, antibiotic, antibody, antigen, dimethylsulfoxide, water/dimethylsulfoxide mixture, agarose, saline solution, dielectric particles, metal particles, aqueous inorganic salt solution, nitrocellulose gel, sol gel, ceramic composite, DNA-coated particles or nanoparticles, and RNA-coated particles or nanoparticles.

Figure 2:
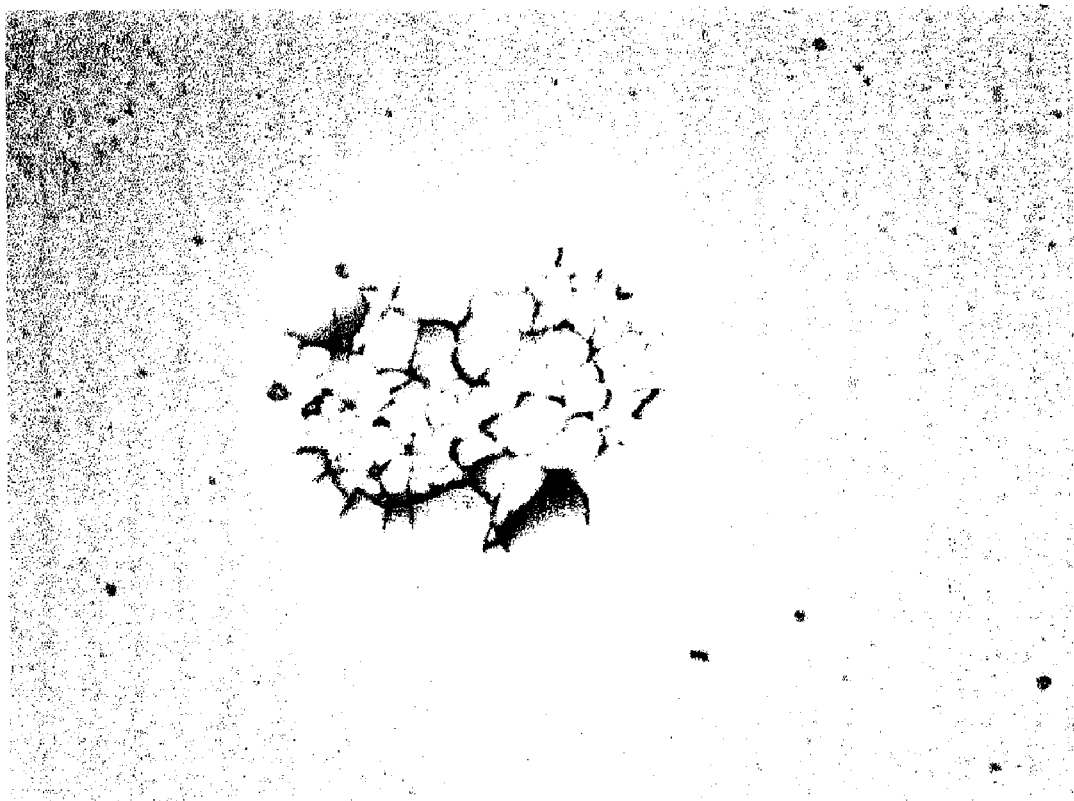
FIG. 2 shows a micrograph of an interlayer that was not removed by a laser pulse.

In some embodiments, the interlayer will remain substantially intact and adhered to the substrate when it absorbs the laser energy. A micrograph illustrating this effect is shown in FIG. 2. The titanium interlayer remained intact, although with mild damage due to rapid heating and cooling. In this case, the mechanism of transfer may be, but is not limited to, photomechanical and/or photothermal shock. This effect may be useful when the biological material to be transferred may be damaged by exposure to higher levels of energy. The laser penetration into the interlayer may be significantly less than the overall layer thickness. Models show that the temperature gain in the interlayer may be about 100-1000 K, but that less than 5% of the transfer material reaches temperatures greater than ambient.

A portion of the biomatrix adjacent to the energized interlayer may be evaporated to cause the transfer. In this case the laser energy is absorbed by the interlayer and rapidly converted into thermal energy. The superheated interlayer then causes flash ablation of a thin, interfacial portion of the biological support layer, which in turn forces jettison of the bulk biological materials. The transfer layer consists of a mixture of the biomaterial and supporting biomatrix.

Figure 3:
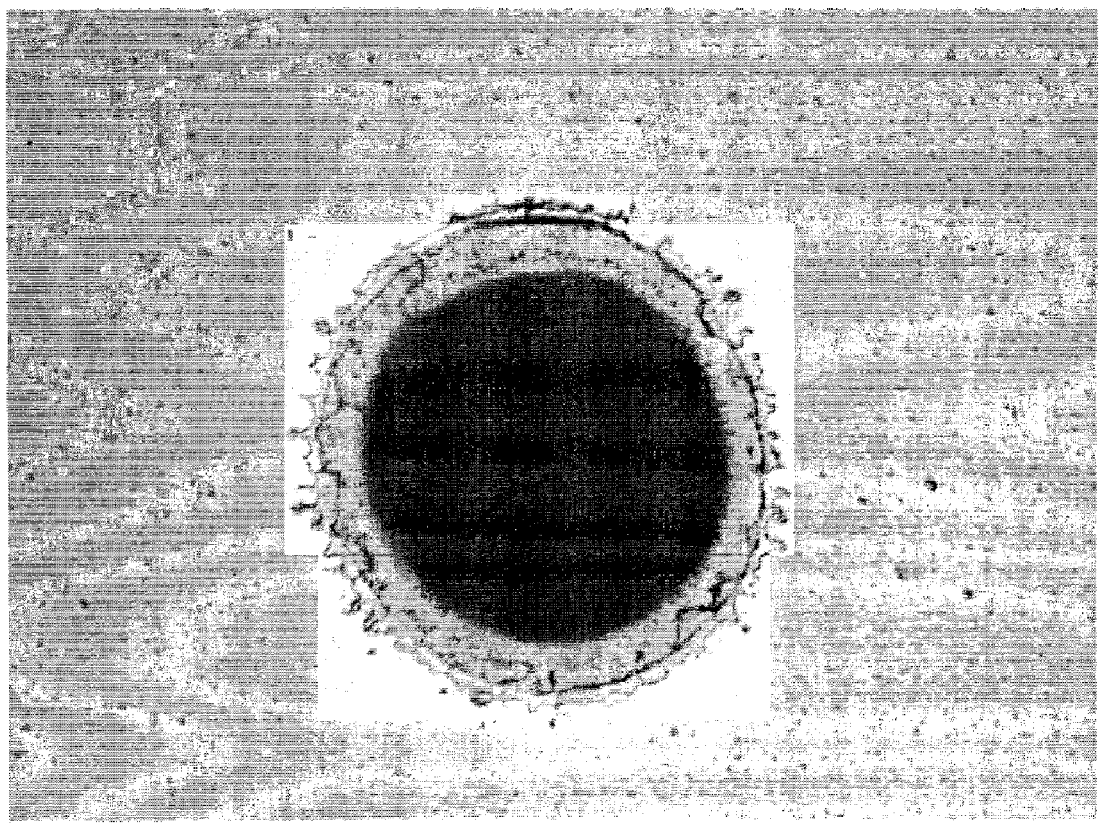
FIG. 3 shows a micrograph of an interlayer that was ablated by a laser pulse.

In some other embodiments, the interlayer may be removed or ablated from the target substrate when it absorbs the photon energy. A micrograph illustrating this effect is shown in FIG. 3. Evidence of explosive removal of the titanium layer can be seen around the edges of the laser-interlayer interaction region. However, this mechanism may be useful when larger portions of a biological material, such as certain entire cells, are transferred. Some cells may be robust enough to withstand such higher levels of energy from the ablated interlayer or from direct exposure to the photon energy. Either mechanism may be appropriate when cells are transferred, depending on the type of cell.

The process can be repeated, exposing additional spots on the target substrate, so that multiple deposits of biological material are formed on the receiving substrate. Multiple target substrates comprising different biological materials may also be used. These deposits may form a pattern, which can have three-dimensional layers. The pattern may have desired properties or perform a desired function, including, but are not limited to, a 2D or 3D cell construct, cell separation, cell isolation, and cell selection. The method may be capable of forming mesoscopic patterns of cells in three-dimensional scaffolds through a layer-by-layer seeding approach.

The invention may improve upon previous cell deposition techniques in terms of accuracy and speed, two components integral to the potential use of cell printing for engineering tissue. While previous work using cell aggregates has, in essence, tried to straddle both traditional tissue engineering methods and the stepwise approach, some studies so far using the invention are focused on the ability to transfer specific types of cells or molecules to specific layers of model tissue scaffolds.

The invention can be capable of building biomaterial constructs in three dimensions through a layer-by-layer approach. This ability separates it from many previous techniques, such as soft lithography, that are excellent for patterning single layers of cells, but are unable to build upon initially deposited layers. With precise deposition techniques, it is possible to build three-dimensional, heterogeneous cell constructs while incorporating growth factors, cytokines and other components, leading to an enhanced framework for tissue growth than traditional, scaffold-based tissues.

For both cell assaying and tissue engineering applications, it is may be necessary to not only deposit large numbers of cells over relatively large (mm) distances, but also to deposit multiple cell types in close proximity to each other. Heterogeneous structures, such as tissues for regenerative medicine applications, are a perfect example of the need to deposit various cell types adjacent to one another. Further applications for adjacent depositions of multiple types of materials include the ability to transfer colonies of stem cells with various other types of "seed" cells, the deposition of growth factors with cells, and improved cell separation methods.

Very few current technologies are able to transition between multiple cell types with efficiency. Applying the invention to produce multi-element arrays can be accomplished by tuning via changes in laser parameters, along with the design of targets with multiple "wells" or separated areas for different types of biological materials. The invention is somewhat unique in that the target can be comprised of multiple wells, each containing a unique cell type or biomaterial. Targets that are 400 mm$^2$ and have as many as 36 1×1 mm$^2$ wells have been designed. This allows for rapid deposition of multiple cell types with no cross-contamination of the various biomaterials (no orifices) or decrease in process efficiency (no need to change heads, lay down additional adhesion layers, or go through different wash cycles, etc). Further, as the system is optically based, it is also possible to use the technique to observe and select certain cell types. The ability to scan a sample and selectively isolate and/or deposit certain cells is very attractive for cell separation experiments and genomics studies.

For protein solutions, the invention can be an alternative to arrayers that use a solid pin or capillary-based fluidics. Protein solutions are typically highly viscous, being prepared in 30-60% glycerol, are strongly adherent to a variety of surfaces and tend to agglomerate at high concentrations. These solutions tend to lead to agglomeration issues with solid pin arraying technologies and clogging and air bubble formation in capillary fluidics with inkjet and quill-pin technologies. Using the present invention, the minimum spot diameter and volume per printed droplet can be, but is not limited to, less at 30 microns and ~500 fL, respectively. The technique may require less than 500 nL of starting material, requires no washing cycles, and deposits spots of protein in a non-contact manner, which can eliminate potential contamination issues.

Models suggest that the laser absorption layer acts as an energy conversion material, converting the radiant laser energy via absorption and conduction into heat, which then flows through the remaining absorption layer to the interface with the protein solution. Calculations of laser penetration into the laser absorption material show that it is significantly less than the total layer thickness, thereby eliminating potential damage to proteins by incident UV radiation. Transient heat conduction models show temperature gains in the laser absorption layer of 1400 K under typical laser and material conditions. The effects of thermal stress upon the solid materials, their spatial displacements and the formation of thermal shock waves are under investigation.

When using nanosecond laser pulses, thermal forces may drive the printing mechanism. The ejection of protein solution away from the target may occur as a result of heat transfer through the absorption interlayer and subsequent vaporization of a portion of the protein solution in direct contact with the heated layer. The calculations discussed above support this prediction, as the absorption layer temperatures are raised above the vaporization temperature for protein solutions. Alternatively, by utilizing near-ultrafast laser pulses, laser forward transfer experiments may be driven by mechanical forces, namely shock waves.

To measure the risk of UV exposure to the biomaterial during the printing process, the percentage of UV laser energy that is absorbed in the metal and metal oxide interlayer film was calculated. Biomaterial transfer is achieved by focusing the laser at the interface of the laser absorption layer and the optically transparent support layer. The exponential absorption coefficient is based upon the calculated penetration depth (skin depth) for the metal. The calculated skin depths at 266 nm for the two metals used as targets are given in Table 1.

TABLE 1

| Interlayer material | Interlayer thickness | Conductivity ($\sigma$) ($\Omega^{-1}$ m$^{-1}$) | Skin Depth ($\delta$) (nm) |
|---|---|---|---|
| Au | 35 nm | 4.5e7 | 2.2 |
| Ti | 75 nm | 2.4e6 | 9.7 |
| TiO$_2$ | 85 nm | — | 10.5[1] |

[1]Skin Depth for TiO$_2$ calculated from $\delta = 1/\alpha$, $\alpha = 4 \cdot \pi \cdot k/\lambda$, k = 2 (average of k⊥ and k∥)

The metal layer thickness used on the targets is much greater than the skin depths. Thus, greater than 99.9% of the non-reflected incident laser energy is absorbed by the solid metal prior to arriving at the absorption layer-biomaterial interface. The TiO$_2$ layer also absorbs the radiation at 266 nm as indicated by the estimated "skin depth" ($\delta \equiv 1/\alpha$) calculated from the complex index of refraction (n+ik) and the absorption coefficient ($\alpha \equiv (4 \cdot \pi \cdot k)/\lambda$). Using this calculation, it is estimated that greater than 99.9% of the incident laser energy is also absorbed by the TiO$_2$ absorption layer prior to any interaction with the biomaterial.

Figure 10:
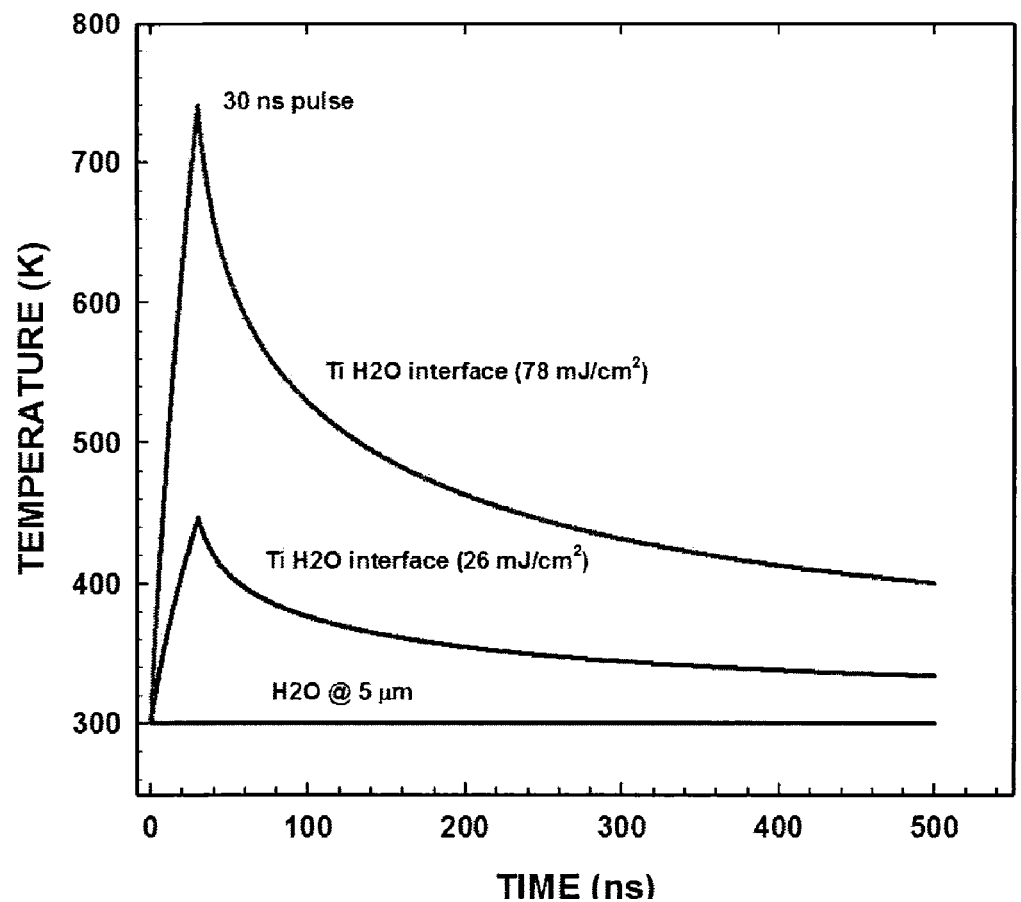
FIG. 10 shows a graph of calculated temperature versus time for a titanium interlayer/biolayer interface and for the middle of a 10 μm aqueous biolayer following a 30 ns laser pulse.

In order to understand the role of heat transfer during the process, the energy transfer from the laser to the laser absorption layer was modeled by the time-dependent heat-transfer equation (parabolic formulation) with a source function given by the Lambert-Beer Law. The composite material heat-conduction equation was solved with a finite-element software package (FlexPDE). The models suggest that the laser absorption layer acts as an energy conversion material, converting the radiant laser energy via absorption and conduction into heat, which then flows through the remaining absorption layer to the interface with the biolayer. The process may be a completely interfacial phenomenon. Calculations of laser penetration into the laser absorption material show that it can be significantly less than the total layer thickness. Transient heat conduction models of laser irradiation of the laser absorption layer show temperature gains in the laser absorption layer from 150 to 450 K, increasing with laser fluence (FIG. 10). Heat transfer through the laser absorption layer showed little dependence on absorption material thickness, as long as the thickness of the absorption layer was greater than the penetration depth (skin depth) of the laser. The effects of thermal stress upon the solid materials, their spatial displacements and the formation of thermal shock waves are under investigation.

Figure 11:
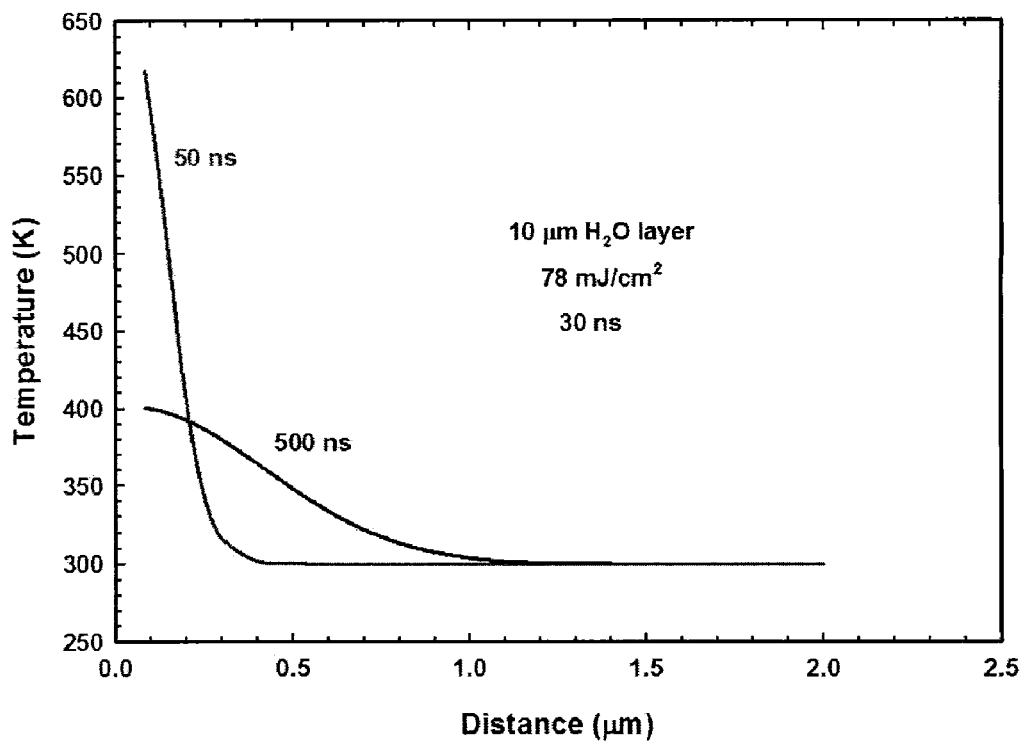
FIG. 11 shows a graph of calculated thermal penetration into a 10 μm aqueous biolayer.

In contrast to the rapid energy conversion and transfer seen in the laser absorption layer, thermal penetration into the much thicker aqueous biomaterial layer (10 to 100 μm thick) is observed to be negligible. FIG. 11 shows the thermal penetration into the biolayer as a function of distance at 50 and 500 ns after laser irradiation. As can be seen in the graph, at 50 ns post-irradiation, thermal penetration is calculated to be less than 400 nm into the biolayer. Even 500 ns post-irradiation, the penetration is only 1.2 μm into the biolayer. This has been observed experimentally as well, when frozen crystals have been observed to be printed onto a room temperature substrate from a frozen target support. Further, this model is an upper limit for thermal penetration, as it uses an insulation model that does not allow for thermal cooling. In addition, the model does not account for the vaporization of the material that would occur as soon as the biomaterial at the interface reaches 400 K. Vaporization at the interface will reduce the amount of thermal penetration by acting as an insulation layer and by reducing the ambient heat via heat of vaporization. While the current model predicts that the first 5% of the material nearest the interlayer is affected, it is likely that the amount of material actually affected is much less. Therefore, it is predicted that fluids printed by this technique will incur little heating, minimizing the potential for denaturing proteins during the printing process. The transfer of the solution may exhibit jetting phenomena as disclosed in U.S. patent application Ser. No. 10/237,072 (issued as a U.S. Pat. No. 6,815,015) to Young et al., filed Sep. 9, 2002 and incorporated herein by reference.

Having described the invention, the following examples are given to illustrate specific applications of the invention. These specific examples are not intended to limit the scope of the invention described in this application.

The apparatus was composed of an optical setup designed to direct a pulsed laser (either a Continuum Mini-lite quadrupled Nd:YAG (266 nm, 3-5 ns FWHM, $E_{max}$=4 mJ, rep rate=1-15 Hz) or MPB Technologies PSX-100 Excimer Laser 248 nm, 2.5 ns FWHM, $E_{max}$=5 mJ, rep rate=0.1-100 Hz) onto a "target" where transfer of a protein solution occurs. The laser was split by a ⅛ beam splitter to an energy meter (Molecutron Max500). The rest of the beam traveled to a UV reflective mirror and directed down (−Z) to a 10× microscope objective (LMU-10X-UVR, OFR, Inc.). The microscope objective focused the laser onto the target, which held the biomaterial to be transferred, and allowed for observation of the transfer process via a confocally aligned CCD camera (Sony DFW-V500). The microscope objective was attached to a micrometer, enabling changes to the focus and observation of the receiving substrate. Protein microarrays were formed by timing laser pulses in conjunction with the movement of the substrates by computer-controlled stages.

The target consisted of an optically transparent quartz disk that was coated with a metal or metal oxide via standard ion assisted electron beam processing techniques (Thin Films Research, Boston, Mass.). Either Au (thickness=300 or 1000 Å) or Ti (750 Å) metals or $TiO_2$ (850 Å) was used as a laser absorption material. To print patterns of proteins, a 0.5 to 5 μL aliquot of protein solution was spread homogeneously on top of this laser absorption layer. Control of the thickness of the biomaterial or protein solution on the target was achieved by using either SU-8 photoresist or 3M PTFE Film Tape #63 over the metal or metal oxide film to produce a 20-100 μm deep well. Well sizes varied from 1 $mm^2$ to 4 $cm^2$, and targets have been fabricated that contained between 4 and 36 wells. The coated target was then placed in the apparatus, where computer control allowed for selective deposition of protein droplets. The multi-welled target allowed for deposition of multiple protein solutions without the need to remove, replace, or wash/rinse the target.

Receiving substrates used for cell depositions were standard glass slides 1"×3" coated with 50-200 μm of commercial basement membrane gel (MATRIGEL™ matrix, BD Biosciences). The gel was deposited as a liquid on the slide and mechanically bladed to the required thickness. Substrates for protein transfers were silinated glass microscope slide used as acquired (BD Biosciences). Ribbon to substrate distances were approximately 500 μm for cell transfers and 250 μm for protein solution transfers.

The target and the receiving substrate were on independent computer-controlled XY translation stages (Aerotech ATS36210, Aerotech ATS15030) with maximum translation speeds of 200 and 75 mm/s, respectively. While deposition rates were currently limited by laser repetition rates (100 or 15 Hz), these stages allowed a theoretical limit of 22,500 transfers/minute with 100 μm diameter spots spaced 100 μm apart. Significantly higher deposition rates are therefore possible with an alternative laser running in the near kHz range. The receiving substrate was on a manual Z translation stage (Newport) which allowed for ½" of vertical travel to adjust for varying types of receiving substrates.

EXAMPLE 1

Deposition of Eukaryotic Cells in a Large-Scale Array Format

Figure 7:
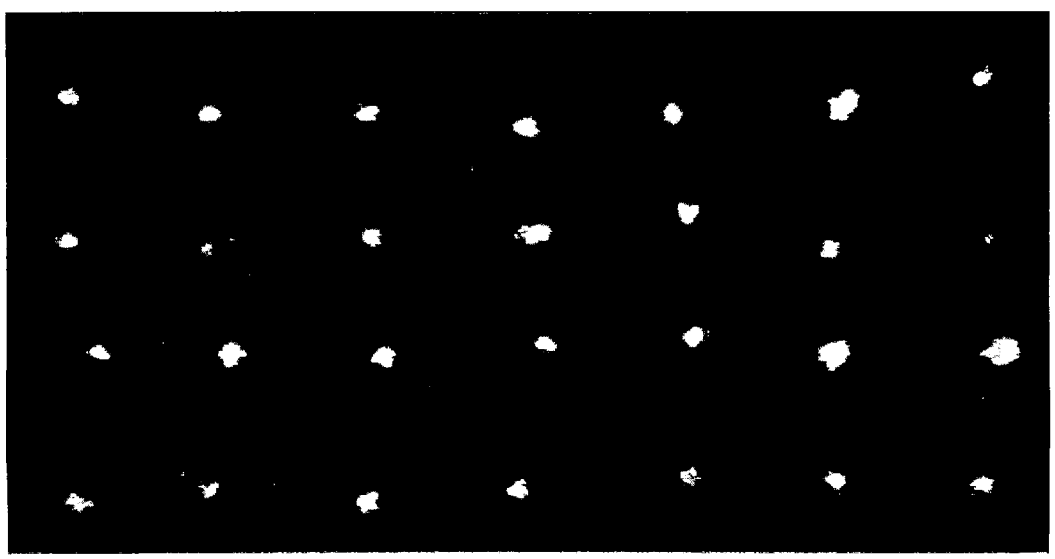
FIG. 7 shows a fluorescence micrograph of a large-scale array of transferred human osteosarcoma cells.

Human osteosarcoma cells (ATCC #: CRL-1427, designation: MG-63) were cultured as per literature, trypsinized and placed in a deposition media composed of 50% (v/v) DMEM, 45% (v/v) Fetal Bovine Serum and 5% glycerol (v/v). Cell concentration in the deposition media was found to be $10^6$ cells/mL. 12 μL of the deposition solution was spread across a 4 $cm^2$ area of the target and then placed in the apparatus for transfer. Arrays of cell were deposited onto 1×3" glass slides coated with a 200 μm thick Matrigel™ basement membrane matrix, immersed in DMEM and placed in an incubator 5 minutes after transfer. Twenty hours post-transfer, the cells were washed with 1×PBS and assayed via a live/dead viability/cytotoxicity kit (Molecular Probes, L-3224) (FIG. 7).

In this deposition, the laser spot was 100 μm in diameter at the laser absorption interface and laser fluence was 160 mJ/$cm^2$. Deposition spots were approximately 100 μm in diameter and spaced 600 μm apart. Initial cell concentrations on the receiving substrate were approximately 3-10 cells per deposition spot, which correlates with cell concentrations in the target solution ($10^6$ cells/mL) and the calculated volume of the material transferred (3-10 pL/spot). Live/dead assays show that cell viability was near 100% 20 hours post-deposition. Several cell lines (ATCC designations: MG-63, EOMA GFP, C2C12, P19) have been printed and show near 100% viability when deposited with both laser systems (Nd:YAG and XeF excimer) and with several types of laser absorption layers ($TiO_2$, Ti, Au). For feasibility studies of the invention as an arraying technology, homogeneous arrays of MG63 cells with overall array areas of 20 mm by 20 mm and deposition rates of 100 spots/s have been deposited.

Cell viability was tested with a live/dead viability kit (L-3224, Molecular Probes) consisting of two dyes: live test by calcein AM (dye 1, 10 µM, ex/em ~495 nm/515 nm) and membrane exclusion test by ethidium homodimer-1 (dye 2, 10 µM, ex/em ~495 nm/635 nm). Images of transferred cells were obtained with a Hitachi HV-C20M CCD camera attached to a Nikon Optiphot-2 microscope with an epifluorescent attachment after 30 min of incubation in the viability assay solution.

EXAMPLE 2

ATCC Designation MG 63 Human Osteosarcoma Cells and C2C12 Mouse Myoblast Cells

Figure 4:
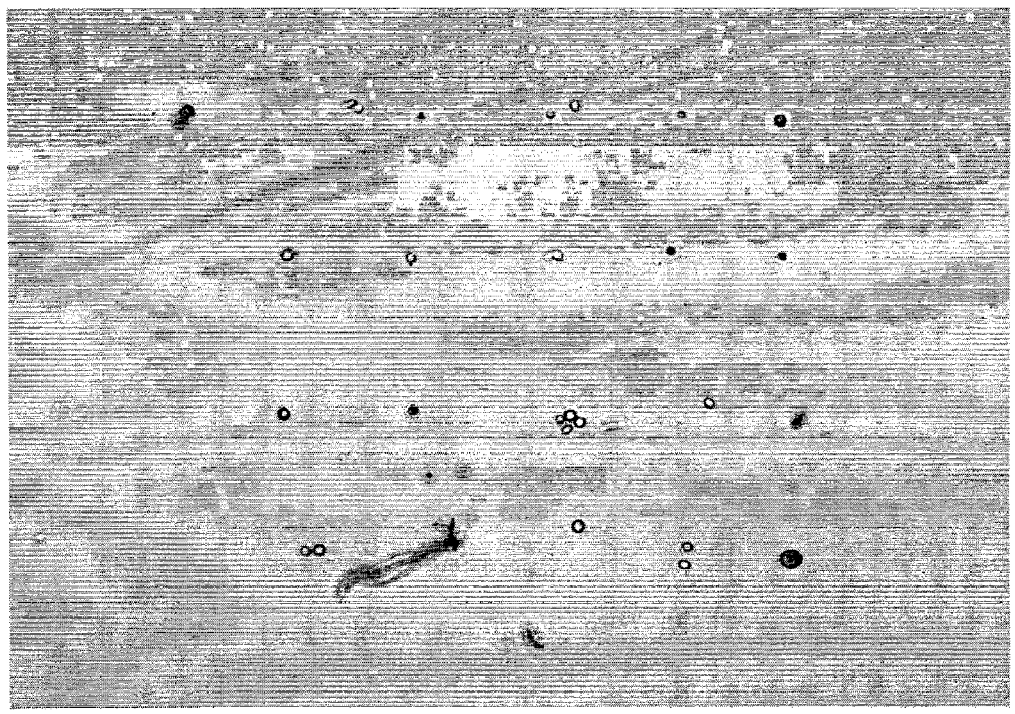
FIG. 4 shows a micrograph of transferred cells.

MG63 cells were initially obtained from ATCC (USA) and cultured in 5% humidified $CO_2$ in air at 37° C. in Dulbecco's Modified Eagle Medium (DMEM) with high glucose, 10% (v/v) fetal bovine serum, and 1% (v/v) streptomycin. FIG. 4 shows a patterned row of cells transferred from a titanium-coated quartz support and deposited onto a quartz substrate coated with matrigel (50 µm). The apparatus was as described above. By varying laser spot size, the number of cells deposited could be controlled. At ~100 µm spot size and an energy of 0.35 µJ/pulse, near-single cell transfers were obtained, at cell transfer rate of 1 cell/shot (±0.5). Laser fluence was 4.4 mJ/cm$^2$.

EXAMPLE 3

ATCC Designation MG 63 Human Osteosarcoma Cells

Human osteosarcoma cells along with 10 µm fluorescent beads were transferred from a titanium-coated quartz support using the energy conversion method. The cells and beads were in a 25% glycerol, 25% cell media (DMEM), and 50% aqueous bead (0.15 M NaCl, 0.05% Tween 20, 0.02% thimerosal) solution. Laser fluence was 160 mJ/cm$^2$ and spot sizes were 100 µm in diameter.

EXAMPLE 4

Verification that Cells are not Stressed

Certain cells can express heat shock proteins (i.e. HSP60, HSP70, etc.) during and after exposure to various stressors including elevated temperature and shear conditions. Immunocytochemical staining experiments (primary antibody: mouse anti-HSP60/HSP70, secondary antibody: fluorescein anti-mouse) were performed using MG63 osteosarcoma cell exposed to elevated incubator temperatures (45° C.) for one hour, normal incubation conditions, and cells printed by the present process. A low level of fluorescence emanated from laser printed cells, similar to or lower than that from the negative control cells. This implies that laser-printed cells did not experience significant enough levels of stress during the printing process to express proteins known to be markers for heat and shear stress.

EXAMPLE 5

Multiple Cell Types

Figure 12A:
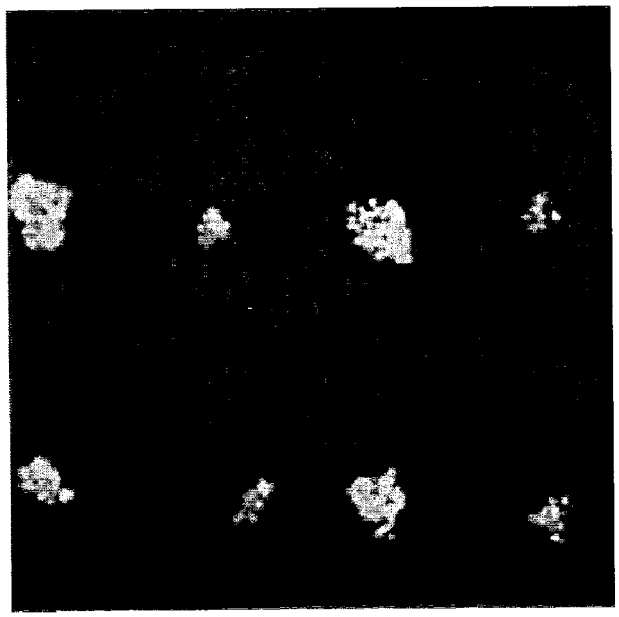
FIG. 12 shows fluorescence micrographs of human osteosarcoma cells and mouse endothelial cells.
Figure 12B:

Human osteosarcoma cells (MG-63) were deposited in an array format on a basement membrane with 800 µm spacing between spots. An array of mouse endothelial cells (ATCC #: CRL-2587, designation: EOMA GFP) was then transferred to the same substrate, but offset 400 µm. The substrate was incubated post-transfer for 24 hours, and then tagged with DAPI nuclear stain (ex: 369 nm, FIG. 12(a)). FIG. 12(a) shows that both cell types have taken up the nuclear stain and show strong blue fluorescence at 465 nm. The EOMA cells can be optically differentiated from the osteosarcoma cells due to genetic modifications that enable the expression of green fluorescent protein. FIG. 12(b) is a UV micrograph showing fluorescence at 510 nm emanating from the GFP expressing EOMA cells. Both cell types show expected growth as compared to non-laser transferred controls. Cell concentrations of the MG-63 cell solution on the target ($1.5 \times 10^8$ cells/mL) were higher than the EOMA cell solution ($4.0 \times 10^7$ cells/mL), causing the notable size difference in the transfer spots. This demonstrates the feasibility of using the invention for design of heterogeneous tissues or development of multi-element whole-cell based biosensors.

EXAMPLE 6

Three-Dimensional Scaffold

Figure 5:
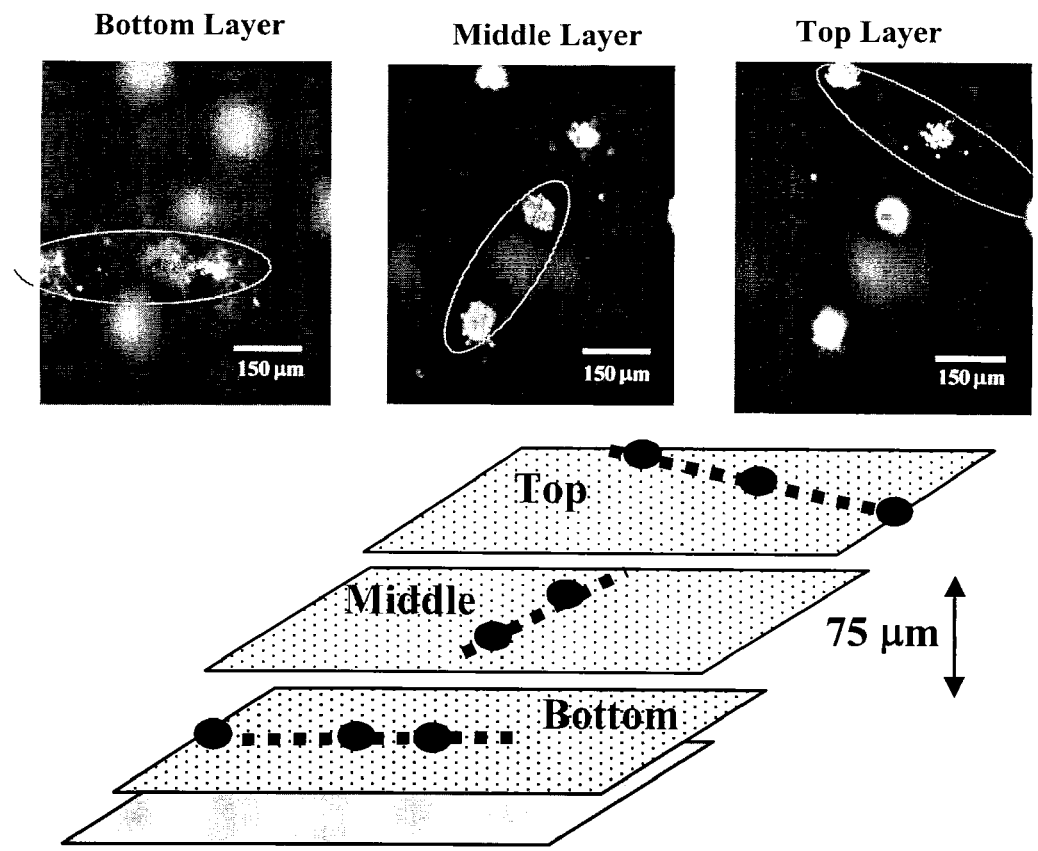
FIG. 5 shows micrographs of and schematically illustrates a seeded three-layer scaffold.

An example of the method's ability to deposit in three dimensions is shown in FIG. 5. A bottom layer of basement membrane (50 µm thick) was spread onto a glass substrate and droplets of MG-63 human osteosarcoma cells were deposited approximately 100-150 µm apart. The slide was removed, and a 75 µm thick layer of basement membrane was spread onto the substrate, and another line of cells was deposited overtop and orthogonally to the first. A third layer of 75 um Matrigel was spread and a third layer of cells was transferred. The cells were then incubated overnight and a live/dead assay was performed (FIG. 7). The cells transferred into the first layer of basement membrane show adhesion and expansion at 24 hours post transfer, as would be expected if they were growing in a 2-D culture vessel. It has been observed that the printing process produces enough forward translational energy that the cells will embed in the receiving gel. Because the first basement membrane layer was relatively thin, the deposited cells were able to pass through this layer, adhere to the glass substrate beneath, and grow. In contrast to the lower layer, the cells deposited into the second and third layers of basement membrane show ball-like growth, common to sarcoma cell lines when the cells are embedded in a matrix with no accessible adherent surface.

EXAMPLE 7

Transfer of Protein Solution

Figure 6A:
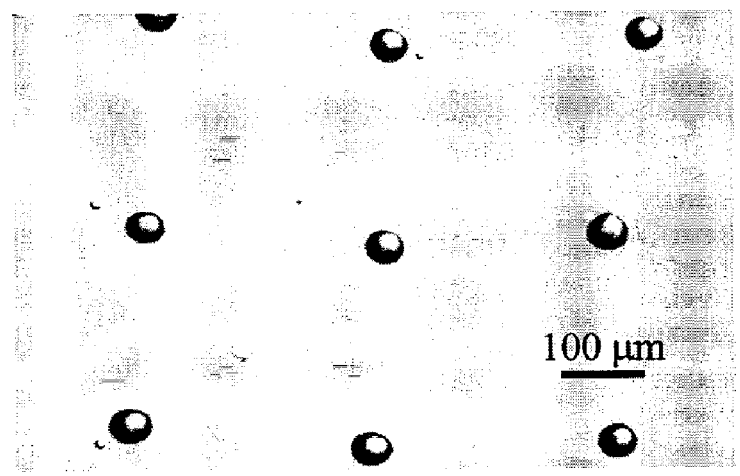
FIG. 6 shows a micrograph of transferred spots of BSA solution.
Figure 6B:
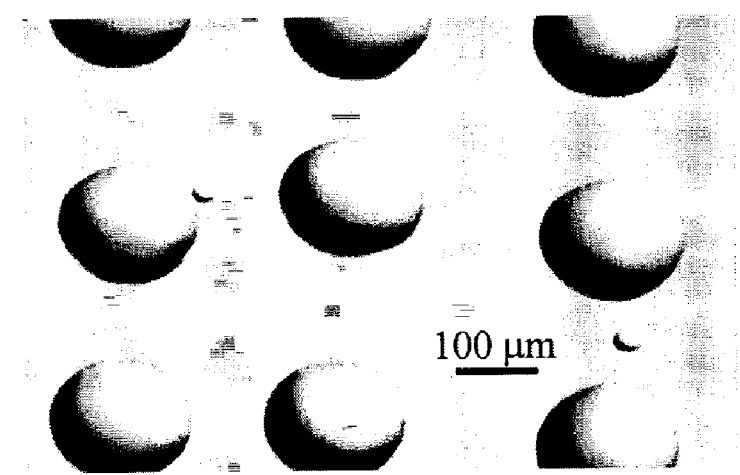

The invention can be capable of depositing volumes of material ranging from hundreds of femtoliters to nanoliters. This capability is demonstrated in FIG. 6 where incident laser energy was varied to change deposited spot size of an aqueous bovine serum albumin (BSA) solution. The solution used in these experiments was composed of 250 ng/μL biotinylated BSA with 0.1% (v/v) sodium dodecyl sulfate and 50% (v/v) glycerol. Volume calculations based on profilometry measurements of deposited material on hydrophilic glass slides show that it is possible to obtain transfer volumes from 1.6 pL (FIG. 6(a)) to 230 pL using laser fluences of 95 mJ/cm$^2$ and 350 mJ/cm$^2$, respectively (FIG. 6(b)). The ability to tune the volume of material transferred over two orders of magnitude may come from the flexibility inherent in the system. By changing the laser energy, the laser focal spot size, and the thickness of the biological material being transferred, it is possible to induce large effects on the resulting printing process.

Reproducibility is a major concern in the development of a biological printing technique. MAPLE DW suffered from difficulty in producing spot-to-spot reproducibility over large areas. Transfer of large-scale arrays of aqueous solutions has shown that it is possible to attain spot diameters with a standard deviation of 9.3% for the spot diameter (N=200, spot diameter=61+/−5.7). This level of error in reproducibility is comparable to other research devices producing much larger spots and is slightly larger than those quoted for standard, commercial-grade piezo-tip and solid pin arrayers. However, it should be possible to reduce the variation in spot size significantly.

EXAMPLE 8

Transfer of Variable Amounts of Protein Solution

Figure 8A:
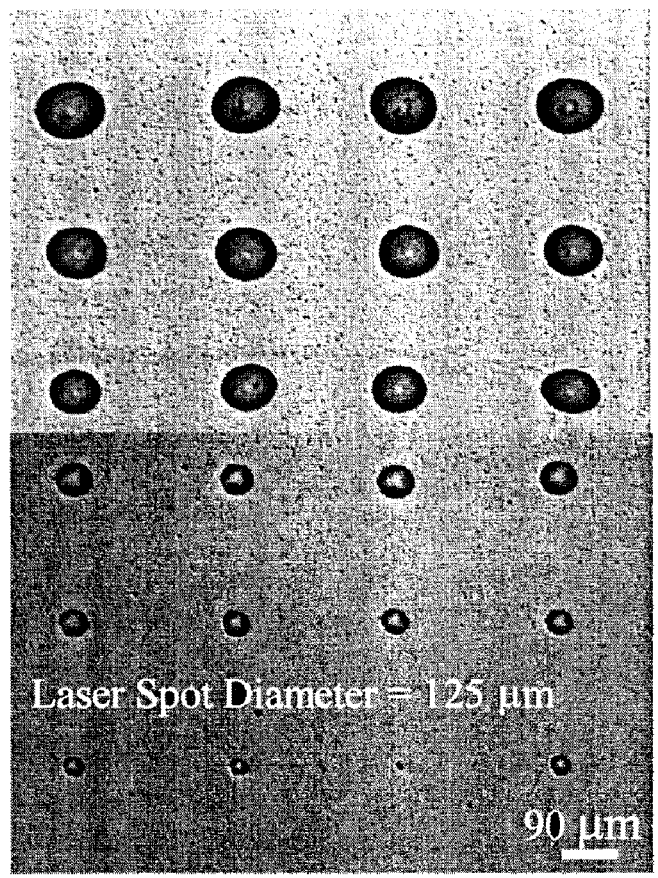
FIG. 8 shows a micrograph of transferred spots of BSA solution and the topology of one spot.

Experiments were performed to determine the adjustability of transfer volume and to quantify the minimal volume capable of being reproducibly transferred. The protein solution used for these experiments was a 1 μg/μL bovine serum albumin (BSA) in 40% (v/v) glycerol, 60% (v/v) phosphate buffer solution (PBS), and 0.5% (w/v) sodium dodecyl sulfate (SDS) to enhance spreading of the solution on the target support. FIG. 8(a) shows a micrograph of a BSA array deposited by increasing the laser fluence from 20 to 50 mJ/cm$^2$ (laser spot diameter=125 μm). Optical microscopy was used to determine the resulting spot areas, and optical profilometry was used to measure the volumes of the printed droplets. Under these laser parameters, droplets with average diameters from 30 to 125 μm were printed, increasing with fluence. Profilometry measurements determined that the transferred protein spots have a contact angle of 5°. The glass slide used in this experiment was wiped clean with methanol, but not cleaned in an acid and/or base bath to expose a truly hydrophilic surface. Therefore, the glass surface is most likely slightly hydrophobic due to environmental and laboratory contaminants (residual alcohol cleaning solutions, dust, salts, etc.). The small contact angle measured by the profilometer is most likely induced by the SDS surfactant present in the protein solution.

Figure 8B:
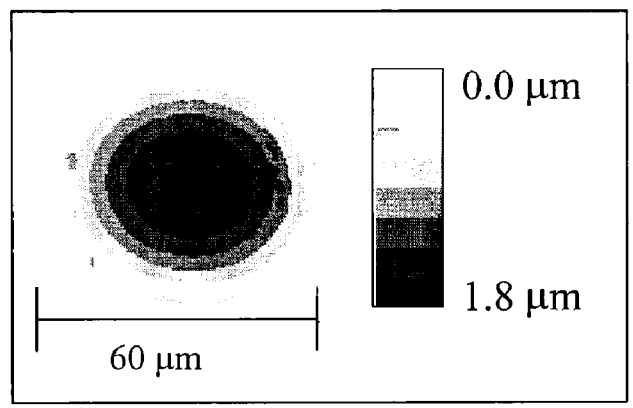

FIG. 8(b) shows a sample topology of one of the deposited droplets, with a calculated volume of 2 pL, a 60 μm diameter, and a contact angle of 5°. Due to limitations of the optical profilometer, accurate measurements could not be made on the 30 μm diameter droplets shown in the bottom row of FIG. 8(a). Based on the volumes calculated for the larger spots, the volume for the 30 μm diameter spots of approximately 500 fL (assuming a similar contact angle) was extrapolated. The volumes of the largest droplets (125 μm diameter) were measured to be 25 pL. It is also possible to use this technique to produce drops with volumes in the nanoliter range by increasing the energy and diameter of the focused laser.

This data demonstrates that under optimal transfer conditions, the invention can have the ability to print aliquots of protein solution with 2.5 times smaller spot sizes and 200 times smaller volumes than piezo-tip printers, which are the commercial-grade arrayers with the smallest demonstrated spot size and volumes. In addition, by simply changing the laser energy, the invention can print a range of volumes of nearly three orders of magnitude. This versatility should enable the invention to generate more dense protein microarrays than commercial arrayers as well as gradient arrays with varying concentrations and protein densities for more quantitative analysis.

EXAMPLE 9

Large Scale Array

Figure 9A:
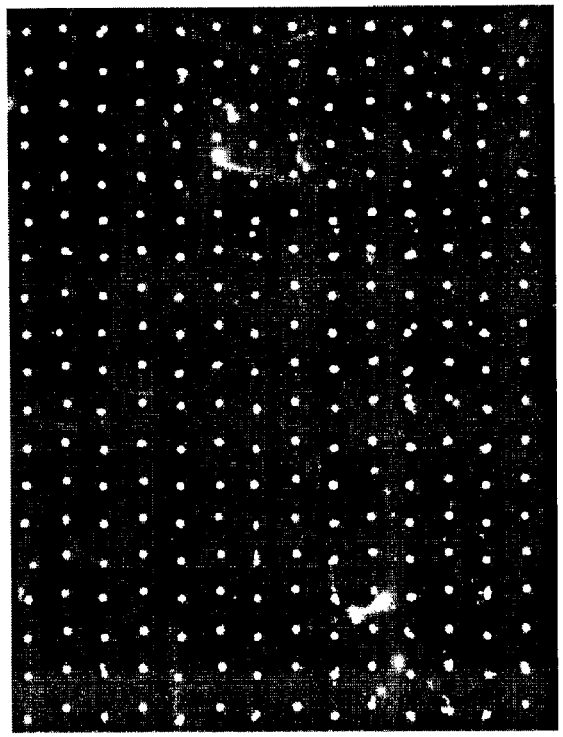
FIG. 9 shows a micrograph of a BSA microarray.
Figure 9B:
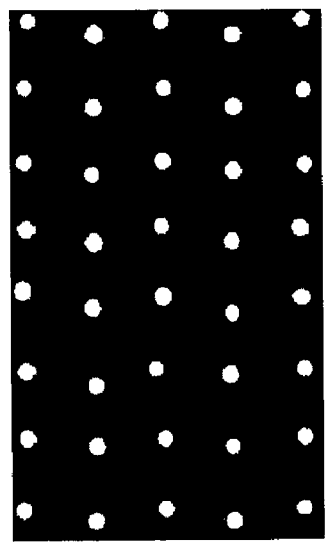

FIG. 9(a) is a fluorescent image of a N=266 spot laser-deposited, biotinylated bovine serum albumin (BSA) array. Droplets of 250 ng/μL biotinylated BSA were first deposited onto a nitrocellulose-coated glass slide (FAST™ slides, Schleicher & Schuell, Keene, N.H.) by the biological laser printer. After blocking the membrane with casein, the slide was exposed to cy5-conjugated streptavidin, and results were then analyzed on a GENEPIX® 4000B microarray scanner (Axon Instruments, Inc.). This laser deposition and fluorescent tagging experiment demonstrated that this approach is able to accurately place biotin-labeled protein onto recipient substrates and assay the presence of bound protein contained in ~3000 □m$^2$ areas. FIG. 9(b) is a higher magnification image showing the reproducibility of the deposition technique. Preliminary results also showed protein activity for the printed enzyme.

The level of reproducibility shown in FIG. 9 is consistent with other research prototype devices transferring larger volumes of protein solution. It should be possible to reduce spot-to-spot variation significantly by using more homogenized fluid films on the target and more sophisticated optics and/or lasers to ensure shot-to-shot energy fluctuations are minimized.

Obviously, many modifications and variations of the present invention are possible in light of the above teachings. It is therefore to be understood that the claimed invention may be practiced otherwise than as specifically described.

We claim:
1. A method for printing materials comprising the steps of:
providing a receiving substrate;
providing a target substrate comprising a photon-transparent support, a photon absorbent interlayer coated on the support, and a transfer material comprising a biological material coated on top of the interlayer opposite to the support;
wherein the interlayer comprises a metal or a metal oxide;
providing a source of photon energy; and
directing the photon energy through the transparent support so that the photon energy strikes the interlayer;
wherein a portion of the interlayer is energized by an absorption of the photon energy; and
wherein the energized interlayer causes a transfer of a portion of the transfer material across a gap between the target substrate and the receiving substrate and onto the receiving substrate.
2. The method of claim 1, wherein the energized interlayer remains intact and adhered to the target substrate.

3. The method of claim 1, wherein the energized interlayer is removed.

4. The method of claim 1,
wherein the transfer mateijal further comprises a biomatrix; and
wherein the transfer occurs through an evaporation of a portion of the biomatrix adjacent to the energized interlayer.

5. The method of claim 4, wherein the biomatrix is a wet solution and the transferred solution evaporates or dries while the solution is in the gap.

6. The method of claim 1, wherein the transfer occurs through a photomechanical shock.

7. The method of claim 1, wherein the transfer occurs through a photothermal shock.

8. The method of claim 1, wherein the transfer occurs through an ablation of the interlayer.

9. The method of claim 1, wherein the photon transparent support comprises quartz.

10. The method of claim 1, wherein the photon transparent support comprises a material selected from the group consisting of a glass, a salt, and a polymer.

11. The method of claim 1, wherein the interlayer comprises a material selected from the group consisting of titanium metal, titanium dioxide, chrome, molybdenum, gold, polymer, and combinations thereof.

12. The method of claim 1, wherein the interlayer is 10 Angstroms to 10 microns thick.

13. The method of claim 1, wherein the receiving substrate comprises a cushioning coating.

14. The method of claim 1, wherein the biological material is selected from the group consisting of eukaryotic cells and prokaryotic cells.

15. The method of claim 1, wherein the biological material is selected from the group consisting of proteins, hormones, enzymes, antibodies, DNA, RNA, nucleic acids, aptamers, antigens, lipids, oligopeptides, polypeptides, cofactors, and polysaccharides.

16. The method of claim 1, wherein the biological material is in a powder form.

17. The method of claim 1, wherein the biological material is a biocompatible organic or inorganic material.

18. The method of claim 1, wherein the transfer material comprises a combination of the biological material and a supporting biomatrix.

19. The method of claim 18, wherein the biomatrix is selected from the group consisting of cell medium, water, glycerol, a mixture of water and glycerol, mammalian serums, buffered salt solution, biocompatible polymers, extracellular matrix, organic tissue scaffolding, inorganic tissue scaffolding, biocompatible surfactants, sodium dodecyl sulfate, cell medium, cell nutrient, natural hydrogel, synthetic hydrogel, surfactant, antibiotic, antibody, antigen, dimethylsulfoxide, water/dimethylsulfoxide mixture, agarose, saline solution, dielectric particles, metal particles, aqueous inorganic salt solution, nitrocellulose gel, sol gel, ceramic composite, DNA-coated particles or nanoparticles, and RNA-coated particles or nanoparticles.

20. The method of claim 18, wherein the biological material is cells.

21. The method of claim 20, wherein the cells are stained.

22. The method of claim 20, wherein the cells are living.

23. The method of claim 22, comprising an additional step of:
lysing the living cells after the transfer of a portion of the transfer material to the receiving substrate.

24. The method of claim 22, wherein the living cells remain living after the transfer of a portion of the transfer material to the receiving substrate.

25. The method of claim 22, wherein the living cells are dead after the transfer to the receiving substrate.

26. The method of claim 20, wherein the cells on the target substrate are dried or lyophilized.

27. The method of claim 18, wherein the photon energy transfers a single cell.

28. The method of claim 1, wherein the photon energy source is a pulsed laser.

29. The method of claim 28, wherein the laser energy has a fluence between 1 and 1000 mJ/cm$^2$.

30. The method of claim 28, wherein the laser energy has a fluence of at least 0.1 mJ/cm$^2$.

31. The method of claim 28, wherein the laser energy has a fluence of at least 1 nJ/cm$^2$.

32. The method of claim 1, wherein the photon energy source is a continuous laser.

33. The method of claim 1, wherein the photon energy source is a flash lamp.

34. The method of claim 1, wherein the photon energy source is a maser.

35. The method of claim 1, wherein the target substrate, the receiving substrate, and the photon energy source are moveable with respect to each other.

36. The method of claim 1, wherein the step of providing a target substrate is repeated one or more times using one or more additional target substrates comprising one or more different transfer materials.

37. The method of claim 1, wherein the directing step is repeated to produce a pattern of transfer material on the receiving substrate.

38. The method of claim 37, wherein the pattern comprises living cells.

39. The method of claim 37, wherein the pattern comprises a plurality of different transfer materials.

40. The method of claim 37, wherein the pattern comprises a plurality of three-dimensional layers.

41. The method of claim 37, wherein the pattern forms a two-dimensional or three-dimensional cell construct.

42. The method of claim 1, wherein the target substrate comprises a plurality of regions comprising different biological materials.

43. The method of claim 1, wherein the method produces a single or multiple element microarray or nanoarray of transfer materials.

44. The method of claim 13, wherein the cushioning coating is at least 10 µm thick hydrogel, at least 10 µm thick polymer, or an aqueous solution.

* * * * *